(12) United States Patent
Ramanathan et al.

(10) Patent No.: US 8,512,559 B2
(45) Date of Patent: Aug. 20, 2013

(54) DEVICE, METHOD, AND SYSTEM FOR SEPARATION AND DETECTION OF BIOMOLECULES AND CELLS

(75) Inventors: Shriram Ramanathan, Portland, OR (US); Chang-Min Park, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 701 days.

(21) Appl. No.: 11/281,891

(22) Filed: Nov. 18, 2005

(65) Prior Publication Data
US 2007/0114180 A1 May 24, 2007

(51) Int. Cl.
*G01N 33/553* (2006.01)
*C02F 1/48* (2006.01)

(52) U.S. Cl.
USPC ............. 210/223; 210/695; 422/73; 436/526; 324/464; 324/207.21; 324/207.11; 435/287.1

(58) Field of Classification Search
USPC ......... 210/222, 223, 695; 436/526; 324/464, 324/207.21, 207.11; 435/287.1; 422/73
See application file for complete search history.

(56) References Cited

U.S. PATENT DOCUMENTS

| | | | | |
|---|---|---|---|---|
| 5,932,097 | A * | 8/1999 | Wilson ........................... | 210/222 |
| 6,468,809 | B1 * | 10/2002 | Prinz et al. .................... | 436/526 |
| 6,726,820 | B1 * | 4/2004 | Frazier .......................... | 204/451 |
| 6,764,861 | B2 * | 7/2004 | Prinz et al. .................... | 436/526 |
| 7,280,322 | B2 * | 10/2007 | Takahashi et al. ......... | 360/324.1 |
| 7,391,091 | B2 * | 6/2008 | Tondra et al. ................. | 257/427 |
| 7,977,111 | B2 * | 7/2011 | Shi et al. ........................ | 436/149 |
| 8,334,147 | B2 * | 12/2012 | Voegeli ......................... | 436/526 |
| 2002/0076825 | A1 * | 6/2002 | Cheng et al. .................. | 436/174 |
| 2002/0142490 | A1 * | 10/2002 | Sato et al. ......................... | 438/3 |
| 2002/0166800 | A1 * | 11/2002 | Prentiss et al. ............... | 209/214 |
| 2003/0040129 | A1 * | 2/2003 | Shah ............................. | 436/526 |
| 2005/0100930 | A1 * | 5/2005 | Wang et al. ....................... | 435/6 |

OTHER PUBLICATIONS

Choi et al., A new magnetic bead-based, filterless bio-separator with planar electromagnet surfaces for integrated bio-detection systems, 2000, Elsevier Sicne S.A., Sensors and Actuators B68, p. 34-39.*
Kim et al., The fabrication of high sensitive spin-valve sensor for magnetic bead detection, May 21, 2004, Wiley, pp. 1961-1964.*
Li et al., Spin valve sensors for ultrasensitive detection of superparamagnetic nanoparticles for biological applications, Nov. 2, 2005, Elsevior, Journal of Sensors and Actuators, pp. 98-106.*

(Continued)

*Primary Examiner* — David C Mellon
(74) *Attorney, Agent, or Firm* — Pillsbury Winthrop Shaw Pittman LLP

(57) ABSTRACT

Embodiments of the invention relate to device, method, and system for separation and/or detection of biological cells and biomolecules using micro-channels, magnetic interactions, and magnetic tunnel junctions. The micro-channels can be integrated into a microfluidic device that may be part of an integrated circuit. Magnetic interactions used for the separation are created, in part, by magnetic stripes associated with the micro-channels. Detection of biological cells and biomolecules is effectuated by a magnetic tunnel junction sensor that comprises two ferromagnetic layers separated by a thin insulating layer. The magnetic tunnel junction sensor can be integrated into a silicon based device, such a microfluidic device, an integrated circuit, or a microarray to achieve rapid and specific separation and/or detection of biomolecules and cells.

29 Claims, 5 Drawing Sheets

Model calculation of detecting a single magnetic particle using a spin tunneling junction sensor.

(56) References Cited

OTHER PUBLICATIONS

Ferreira et al., Biodetection using magnetically labeled biomolecules and arrays of spin valve sensors (invited), May 15, 2003, Journal of Applied Physics, vol. 93, No. 10, pp. 7281-7286.*

Graham et al., Magnetoresistive-based biosensors and biochips, Sep. 2004, Trends in Biotechnology, vol. 22, No. 9, pp. 455-462.*

Carey et al., Spin valves using insulating cobalt ferrite exchang-spring pinning layers, Aug. 5, 2002, Applied Physics Letters, vol. 81, No. 6, pp. 1-3.*

Shen et al., In situ detection of single micron-sized magnetic beads using magnetic tunnel junction sensors, Jun. 16, 2005, Applied Physics Letters, 86, 253901, pp. 1-3.*

* cited by examiner

FIG. 1. Top-down view and cross-section view of a micro-channel and associated electromagnet for separating magnetically tagged biomolecules.

FIG. 2. Spin tunneling junction sensor for detecting magnetically tagged biomolecules.

FIG. 3  Model calculation of detecting a single magnetic particle using a spin tunneling junction sensor.

FIG. 4   Separation and detection in a single device

US 8,512,559 B2

DEVICE, METHOD, AND SYSTEM FOR SEPARATION AND DETECTION OF BIOMOLECULES AND CELLS

RELATED APPLICATIONS

None.

FIELD OF INVENTION

The embodiments of the invention relate to devices, methods, and systems for the separation and/or detection of biological cells and biomolecules. More specifically, the embodiments relate to devices, methods, and systems for on-chip separation of biological cells and biomolecules using magnetic and microfluidic technologies, and to the detection of biomolecules or cells using a magnetic tunnel junction sensor. The invention transcends several scientific disciplines such as physics, engineering, material science, biochemical analysis, and molecular biology.

BACKGROUND

The separation and detection of biological cells and biomolecules, such as red blood cells, white blood cells, platelets, proteins, DNAs, and RNAs, have become more and more important to biological assays crucial to fields such as genomics, proteomics, diagnoses, and pathological studies. For example, due to faster and more specific methods of separating and detecting cells and biomolecules, the molecular-level origins of disease are being elucidated at a rapid pace, potentially ushering in a new era of personalized medicine in which a specific course of therapy is developed for each patient. To fully exploit this expanding knowledge of disease phenotype, new methods for separating and detecting multiple cells and biomolecules (e.g., DNA and proteins) simultaneously are required. In many cases, separation and detection of a single molecule or a DNA fragment are desirable or required. Thus, cell or biomolecule separation and detection devices and methods should be rapid, sensitive, target specific, highly parallel, and/or comprehensive.

A specific type of cell and biomolecule separation and detection method uses microfluidic devices to conduct high throughput separation and analysis. By designing patterned fluidic channels in the micro or sub-micro scales, often on a small chip, one is able to carry our multiple assays simultaneously. The cells and biomolecules in microfluidic assays typically are detected through optical readout of fluorescent labels attached to a target cell or molecule that is specifically attached or hybridized to a probe molecule. Separation technologies currently used for biomolecules, such as nucleic acid and protein, typically utilize gel electrophoresis or microfluidic channels which typically employ incorporated fluorescent labels or dyes.

Some biomolecule detection methods have been developed based upon the unique electrochemical and photoelectrochemical properties of metal particles. In one assay method, gold nanoparticles (approximately 10 nm diameters) are tagged with ssDNA probe strands and a photoactive dye molecule. A metal electrode of a microarray chip (also called gene chip) is also modified with ssDNA probe strands. If a target (the analyte or bioanalyte) mRNA or ssDNA is complementary to the probe on the particle and the substrate, hybridization will occur which brings the particle in contact with the electrode. A laser is then radiated across the surface. When the laser addresses a spot in which nanoparticles are bound, the dye molecule is electronically excited, and the excited electron is injected into the electrode. The electron is collected as a current, signifying the presence of a particular DNA analyte.

Synthesis of a functionalized electrode having polymer arrays on an electrode of a microarray chip is known. Examples of such polymer arrays include nucleic acid arrays, peptide arrays, and carbohydrate arrays. One method of preparing functionalized electrodes of polymer arrays on microarray chips involves photolithographic techniques using photocleavable protecting groups. Briefly, the method includes attaching photoreactive groups to the surface of a substrate, exposing selected regions of the substrate to light to activate those regions, attaching a monomer with a photoremovable group to the activated regions, and repeating the steps of activation and attachment until macromolecules of a length and sequence are synthesized.

DETAILED DESCRIPTION

Figure 1:
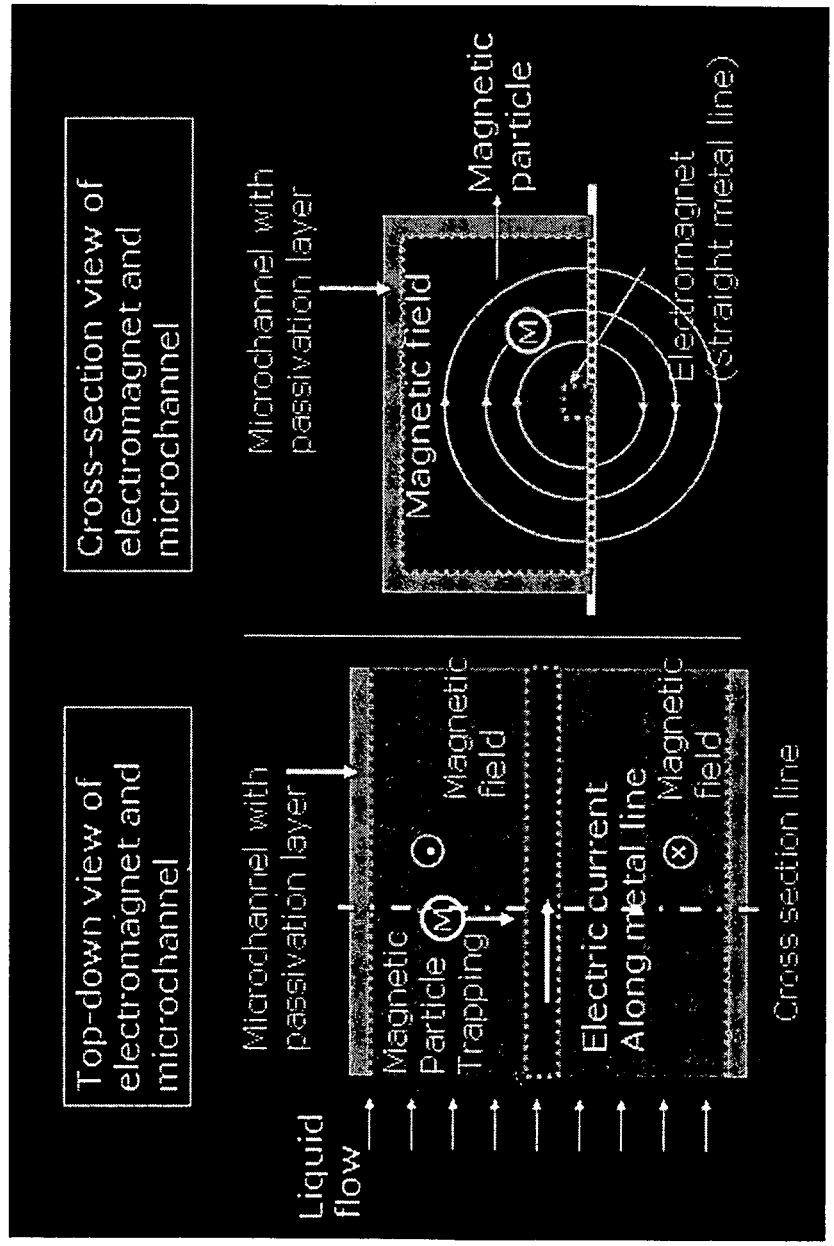
FIG. 1 shows a schematic of a top-down view and a cross-section view of an electromagnet and micro-channel for separating magnetically tagged biomolecules.

An embodiment of the invention relates to separation of biological cells and biomolecules using micro-channels and magnetic interactions. The micro-channels can be integrated into a microfluidic device that may be part of an integrated device, such as a microarray device, a microfluidic device, or an integrated circuit. In the embodiment of the invention, magnetic interactions are created, in part, by magnetic stripes associated with the micro-channels. The magnetic stripes may comprise permanent magnetic materials, ferromagnetic materials, paramagnetic materials, or non-magnetic materials. When ferromagnetic materials are used for the magnetic stripe, an external magnetic field may be applied such that the stripe is magnetized and capable of interactions with magnetically tagged cells and biomolecules. When either a ferromagnetic material or non-magnetic material is used for the stripe, an electrical current may be applied through the stripe, thus creating an electromagnetic stripe that is also capable of magnetic interactions with the magnetically tagged biomolecules or cells.

Another embodiment of the invention relates to a method and device for detecting biological cells and biomolecules using a magnetic tunnel junction sensor. Magnetic tunnel junction, or spin tunneling junction, is known to have applications in spin-electronic devices such as magnetic sensors and magnetic random-access memories (MRAMs). The embodiment of the present invention encompasses using a magnetic tunnel junction sensor to detect magnetically tagged cells and biomolecules. The magnetic tunnel junction sensor comprises two ferromagnetic layers separated by a thin insulating layer. Further, the magnetic tunnel junction sensor can be integrated into a silicon based device, such as a microarray, a microfluidic device and an integrated circuit. The magnetic tunnel junction sensor may be used in conjunction with the micro-channel magnetic separation device disclosed herein so that separation and detection of cells and biomolecules are achieved in a single device.

In the embodiment of the invention, biological cells and biomolecules, which are also referred to as "analytes," are magnetically tagged such that are capable of being separated or detected through magnetic interactions. Conventional methods known to those skilled in the art or methods disclosed herein may be used to tag the analytes. In the embodiment of the invention, fluids containing the analytes are directed and controlled within the microfluidic device and within the micro-channels such that the magnetic interactions between the analytes and the magnetic stripes are capable of being measured and/or monitored to achieve the desired separation and detection.

Analytes in the embodiments of the invention also include proteins, peptides, and, specifically, nucleic acids (DNA and RNA), which can form double-stranded molecules by hybridization, that is, complementary base pairing. In one embodiment of the invention, a molecular probe, such as a DNA probe, is attached to a magnetic tunnel junction sensor, which is immobilized on the surface of, or otherwise integrated into, a microarray. The specificity of nucleic acid hybridization is such that the detection of molecular and/or nanomaterials binding events can be done through measurements of changes in magnetic resistance, magnetoresistance, caused by the interaction of magnetically tagged target molecules (DNA, RNA, proteins, for example.) with the complementary molecular probes (DNA, RNA, anti-body, for example) attached to a magnetic tunnel junction sensor. This specificity of complementary base pairing also allows thousands of hybridization to be carried out simultaneously in the same experiment on a DNA chip (also called a DNA array).

Molecular probes are immobilized on the surface of individual or individually addressable magnetic tunnel junction sensor arrays through the surface functionalization techniques. The Sensors allow polarization and/or magnetoresistance changes to be detected and/or measured. The polymer arrays of the embodiment of the invention could be a DNA array (collections of DNA probes on a shared base) comprising a dense grid of spots (often called elements or pads) arranged on a miniature support. Each spot could represent a different gene.

The probe in a DNA chip is usually hybridized with a complex RNA or cDNA target generated by making DNA copies of a complex mixture of RNA molecules derived from a particular cell type (source). The composition of such a target reflects the level of individual RNA molecules in the source. In the embodiment of the invention, the DNA probe is further tagged with magnetic materials, such as magnetic nano- or micro-particles. The intensities of the signals resulting from the binding events from the DNA spots of the DNA chip after hybridization between the probe and the target represent the relative expression levels of the genes of the source.

The DNA chip could be used for differential gene expression between samples (e.g., healthy tissue versus diseased tissue) to search for various specific genes (e.g., connected with an infectious agent) or in gene polymorphism and expression analysis. Particularly, the DNA chip could be used to investigate expression of various genes connected with various diseases in order to find causes of these diseases and to enable accurate treatments.

Using embodiments of the invention, one could find a specific segment of a nucleic acid of a gene, i.e., find a site with a particular order of bases in the examined gene. This detection could be performed by using a diagnostic polynucleotide made up of short synthetically assembled single-chained complementary polynucleotide—a chain of bases organized in a mirror order to which the specific segment of the nucleic acid would attach (hybridize) via A-T or G-C bonds.

The practice of the embodiments of the invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, detection of hybridization using a label. Specific illustrations of suitable techniques can be had by reference to the example herein below. However, other equivalent conventional procedures can, of course, also be used.

As used in the specification and claims, the singular forms "a", "an" and "the" include plural references unless the context clearly dictates otherwise. For example, the term "a micro-channel" may include a plurality of micro-channels unless the context clearly dictates otherwise.

A "micro-channel" is a channel, groove, or conduit having at least one dimension in the micrometer ($\mu$m), or less than $10^{-3}$ meter (mm), scale. Although micro-channels are typically straight along their length, they may contain angles and curves of different degrees along their length. Although the micro-channels typically have rectangular cross-sections, they may also have other shapes of cross-sections, such as circle. The micro-channels are usually suitable for fluidic communications, such as carrying through a biological liquid. The micro-channels are often part of an integrated device, such a microfluidic device or an integrated circuit such that liquid flowing through the micro-channels are in a controlled pattern and able to be analyzed as desired.

A "closed" micro-channel as used herein refers to a micro-channel that does not contain openings, especially long its length, to the outside except as otherwise provided. A closed micro-channel specifically contrasts an open channel wherein the channel opens to the outside along its length. Micro-channels in the embodiments of the invention may contain openings to facilitate fluid flow or communication through the channels.

As used in the embodiments of the invention, a magnetic stripe is "in association with" or "associated with" a micro-channel when and if the magnetic effect of the magnetic stripe is effectively used to achieve separation of biomolecules and cells within the micro-channel. In other words, each micro-channel is associated with one or more magnetic stripes so that the separation of biomolecules or cells with the micro-channel is facilitated by the associated magnetic stripes. On the other hand, each magnetic stripe is also associated with one or more micro-channels so that the magnetic stripe is capable of facilitating the separation of biomolecules and cells with the micro-channels.

A "microfluidic device" is a device that has one or more micro-channels. A microfluidic device may be part of an integrated device, such as an integrated separation or detection equipment or an integrated circuit. Fluids used in microfluidic devices include whole blood samples, bacterial cell suspensions, protein or antibody solutions and various buffers and saline. Microfluidic devices can be used to obtain many interesting measurements, including fluid mechanical properties, cellular and molecular diffusion coefficients, fluid viscosity, pH values, chemical and biological binding coefficients and enzyme reaction kinetics. Other applications for microfluidic devices include cell and molecule detection and separation, capillary electrophoresis, isoelectric focusing, immunoassays, flow cytometry, sample injection of proteins for analysis via mass spectrometry, DNA analysis, cell manipulation, and cell separation. In the embodiment of the invention, magnetic materials and technologies are incorporated into the microfluidic devices for applications such as cell and biomolecule detection and separation.

The use of microfluidic devices to conduct biomedical assays has many significant advantages. First, because the volume of fluids within these channels is very small, usually several nano-liters, the amount of reagents and analytes required for the assays is quite small. This is especially significant for expensive reagents. The fabrications techniques used to construct microfluidic devices, discussed in more details herein, are relatively inexpensive and are very amenable both to highly elaborated, multiplexed devices and also to mass production, such as in an integrated circuit die. In manners similar to that for microelectronics, microfluidic technologies also enable the fabrication of highly integrated devices for performing different functions on the same substrate chip. Embodiments of the invention helps create integrated, portable clinical diagnostic devices for home and bedside use, thereby eliminating time consuming laboratory analysis procedures.

In the embodiments of the invention, the flow of a fluid through a microfluidic channel, or micro-channel, can be characterized by the Reynolds number (Re), defined as $$Re = LV_{avg}\rho/\mu$$

where L is the most relevant length scale, $\mu$ is the fluid viscosity, $\rho$ is the fluid density, and $V_{avg}$ is the average velocity of the flow. For many micro-channels, including channels with a rectangular cross-section, L is equal to 4A/P where A is the cross-sectional area of the channel and P is the wetted perimeter of the channel. Due to the small dimensions of micro-channels, the Re is usually much less than 100, often less than 1.0. In this Reynolds number regime, flow is completely laminar and no turbulence occurs. The transition to turbulent flow generally occurs in the range of Reynolds No. 2000. Laminar flow provides a means by which molecules can be transported in a relatively predictable manner through micro-channels.

As used herein, "magnetic," "magnetic effect," and "magnetism" refer to the phenomena by which one material exert an attractive or repulsive force on another material. Although theoretically all materials are influenced to one degree or another by magnetic effect, those skilled in the art understand that magnetic effect or magnetism is only recognized for its detectability under the specific circumstance.

As used herein, a "permanent magnet" is a material that has a magnetic field without relying upon outside influences. Due to their unpaired electron spins, some metals are magnetic when found in their natural states, as ores. These include iron ore (magnetite or lodestone), cobalt, and nickel. A "paramagnetic material" refers to a material that attracts and repels like normal magnets when subject to a magnetic field. Paramagnetic materials include aluminum, barium, platinum, and magnesium. A "ferromagnetic material" is a material that can exhibit a spontaneous magnetization. Ferromagnetism is one of the strongest forms of magnetism and is the basis for all permanent magnets. Ferromagnetic materials include iron, nickel, and cobalt. A "superparamagnetic material" is a magnetic material that exhibits a behavior similar to that of a paramagnetic material at temperatures below the Curie or the Neel temperature.

An "electromagnet" is a type of magnet in which the magnetic field is produced by a flow of electric current. The magnetic field disappears when the current ceases. A simple type of electromagnet is a coiled piece of wire that is electrically connected. An advantage of an electromagnet is that the magnetic field can be rapidly manipulated over a wide range by controlling the electric current. In the embodiments of the invention, ferromagnetic or non-magnetic materials are used, e.g., in the form of thin stripes, to form electromagnets.

An "array," "macroarray" or "microarray" is an intentionally created collection of substances, such as molecules, electrodes, detectors and/or sensors, attached to a solid surface, such as glass, plastic or silicon chip forming an array. The arrays can be used to measure the expression levels of large numbers of reactions or combinations simultaneously. The substances in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the pads on the array. A macroarray generally contains pad sizes of about 300 microns or larger and can be easily imaged by gel and blot scanners. A microarray would generally contain pad sizes of less than 300 microns.

A DNA microarray is a collection of microscopic DNA spots attached to a solid surface forming an array. DNA microarrays can be used to measure the expression levels of large numbers of genes simultaneously. In a DNA microarray, the affixed DNA segments are known as probes, thousands of which can be used in a single DNA microarray. Measuring gene expression using microarrays is relevant to many areas of biology and medicine, such as studying treatments, disease and developmental stages.

"Solid support" and "support" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

"Substrate" refers to a material or a combination of materials upon and/or within which other or additional materials are formed, attached, or otherwise associated with according to a predetermined fashion. A substrate often provides physical and functional support to the other or additional materials such that, together, they form part or whole of a functional device. In the embodiments of the invention, the substrate may comprise metal, silicon, glass, or polymeric materials. In more specific embodiments, the substrate comprises an integrated material, such as a microfluidic device or an integrated circuit die.

The term "molecule" generally refers to a macromolecule or polymer as described herein. However, micro-channels or arrays comprising single molecules, as opposed to macromolecules or polymers, are also within the scope of the embodiments of the invention.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either α-, β-, or ω-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

The term "biomolecule" refers to any organic molecule that is part of or from a living organism. Biomolecules include a nucleotide, a polynucleotide, an oligonucleotide, a peptide, a protein, a ligand, a receptor, among others. A "complex of a biomolecule" refers to a structure made up of two or more types of biomolecules. Examples of a complex of biomolecule include a cell or viral particles.

As used herein, "biological cells" and "cells" are interchangeable, unless otherwise clearly indicated, and refer to the structural and functional units of all living organisms, sometimes called the "building blocks of life." Cells, as used herein include bacteria, fungi, and animal mammalian cells. Specifically included are animal blood cells, such as red blood cells, white blood cells, and platelets.

The term "target," "target molecule," or "target cell" refers to a molecule or biological cell of interest that is to be analyzed or detected, e.g., a nucleotide, an oligonucleotide, a polynucleotide, a peptide, a protein, or a blood cell. The target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires and nanoparticles. The target molecule or cell may be magnetically tagged, or labeled to facilitate their detection and separation.

The term "probe" or "probe molecule" refers to a molecule that binds to a target molecule or cell for the analysis of the target. The probe or probe molecule is generally, but not necessarily, has a known molecular structure or sequence. The probe or probe molecule is generally, but not necessarily, attached to a solid support of the mcirofluidic device or array. The probe or probe molecule is typically a nucleotide, an oligonucleotide, a polynucleotide, a peptide, or a protein, including, for example, cDNA or pre-synthesized polynucleotide deposited on the array. Probes molecules are biomolecules capable of undergoing binding or molecular recognition events with target molecules or cells. A probe or probe molecule can be a capture molecule.

The term "capture molecule" refers to a molecule that is immobilized on a surface. The capture molecule is generally, but not necessarily, binds to a target or target molecule or cell. The capture molecule is typically a nucleotide, an oligonucleotide, a polynucleotide, a peptide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. The capture molecule may be magnetically or fluorescently labeled DNA or RNA. In specific embodiments of the invention, the capture molecule may be immobilized on the surface of a magnetic tunnel junction sensor, which itself is part of an integrated device, such as a microfluidic device or an integrated circuit. The capture molecule may or may not be capable of binding to just the target molecule or cell, or just the probe molecule.

The terms "die," "polymer array chip," "DNA array," "array chip," "DNA array chip," or "bio-chip" are used interchangeably and refer to a collection of a large number of probes arranged on a shared substrate which could be a portion of a silicon wafer, a nylon strip or a glass slide.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers."

When the biomolecule or macromolecule of interest is a peptide, the amino acids can be any amino acids, including α, β, or ω-amino acids. When the amino acids are α-amino acids, either the L-optical isomer or the D-optical isomer may be used. Additionally, unnatural amino acids, for example, β-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is a molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex.

The term "chip" or "microchip" refers to a microelectronic device made of semiconductor material and having one or more integrated circuits or one or more devices. A "chip" or "microchip" is typically a section of a wafer and made by slicing the wafer. A "chip" or "microchip" may comprise many miniature transistors and other electronic components on a single thin rectangle of silicon, sapphire, germanium, silicon nitride, silicon germanium, or of any other semiconductor material. A microchip can contain dozens, hundreds, or millions of electronic components. In the embodiments of the invention, as discussed herein, micro-channels, microfluidic devices, and magnetic tunnel junction sensors can also be integrated into a microchip.

"Micro-Electro-Mechanical Systems (MEMS)" is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components could be fabricated using compatible "micromachining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms", to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, unprecedented levels of functionality, reliability, and sophistication can be placed on a small silicon chip at a relatively low cost. In the embodiments of the invention, as discussed herein, MEMS devices are further integrated with micro-channels, microfluidic devices, and/or magnetic tunnel junction sensors, such that, together, they perform separation and detection function for biological cells and biomolecules.

"Microprocessor" is a processor on an integrated circuit (IC) chip. The processor may be one or more processor on one or more IC chip. The chip is typically a silicon chip with thousands of electronic components that serves as a central processing unit (CPU) of a computer or a computing device.

A "nanomaterial" as used herein refers to a structure, a device or a system having a dimension at the atomic, molecular or macromolecular levels, in the length scale of approximately 1-1000 nanometer (run) range. Preferably, a nanomaterial has properties and functions because of the size and can be manipulated and controlled on the atomic level.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The terms "magnetic tunnel junction," "spin tunneling junction" and "magnetic tunnel junction sensor" are used interchangeably to refer to a device or a combination of materials that comprises two ferromagnetic metal layers separated by a thin insulating layer. The insulating layer is so thin, usually a few nanometers, that electrons can tunnel through the insulating layer when a bias voltage is applied between the two ferromagnetic metal layers. In such cases, the two metal layers are also called electrodes. One of the ferromagnetic layer or electrode is called the top electrode as it is often the electrode closer to the detected objects. The other electrode is often called the bottom layer or the bottom pinned layer as it is often the layer closer to the substrate or support the sensor is attached to.

An important property of a magnetic tunnel junction is that the tunneling current depends on the relative orientation of the magnetizations of the two ferromagnetic layers, which can be changed by an applied external magnetic field. This phenomenon is called tunneling magnetoresistance. In the embodiments of the invention, when a magnetically tagged cell or biomolecule is within the detectable distance of the magnetic tunnel junction, the changes in the magnetoresistance are measured to confirm the presence of the cell or biomolecule.

One embodiment of the invention relates to a microfluidic device that comprises a substrate and a closed micro-channel formed on a surface of the substrate. The micro-channel has at least two openings for fluidic communication. The device further comprises a magnetic stripe that extends along the length of the micro-channel and is formed in association with the micro-channel.

Another embodiment of the invention relates to a method of making a device, especially a device for separation and detection of biomolecules using magnetism and microfluidic technologies. The method comprises providing a substrate; fabricating a closed micro-channel having at least two openings for fluidic communication on a surface of the substrate; and fabricating a magnetic stripe extending along the length of the micro-channel and in association with the micro-channel.

The substrate used in the embodiments of the invention may comprise various materials including, but not limited to silicon, glass, metal, and polymeric material. Silicon is a suitable material for forming micro-channels coupled with microelectronics or other microelectromechanical systems (MEMS). It also has good stiffness, allowing the formation of fairly rigid microstructures, which can be useful for dimensional stability. In a specific embodiment of the invention, the substrate comprises an integrated circuit (IC), a packaged integrated circuit, and/or an integrated circuit die. For example, the substrate may be a packaged integrated circuit that comprises a microprocessor, a network processor, or other processing device. The substrate may be constructed using, for example, a Controlled Collapse Chip Connection (or "C4") assembly technique, wherein a plurality of leads, or bond pads are internally electrically connected by an array of connection elements (e.g., solder bumps, columns).

The substrate of the embodiments of the present invention is suitable for forming micro-channels thereon for fluidic communications. The micro-channels may be open or closed along their lengths. Various methods may be used to form the micro-channels on the substrate. For example, an open micro-channel can be fabricated on a silicon substrate by etching methods known to those skilled in the art. Closed micro-channels can be formed by sealing the open channels at top using methods such as anodic bonding of glass plates onto the open micro-channels on the silicon substrate.

According to one embodiment of the invention, to fabricate a micro-channel on a silicon substrate, a photoresist (positive or negative) is spun onto the silicon substrate. The photoresist is exposed to UV light through a high-resolution mask with the desired device patterns. After washing off the excessive unpolymerized photoresist, the silicon substrate is placed in a wet chemical etching bath that anisotropically etches the silicon in locations not protected by the photoresist. The result is a silicon substrate in which micro-channels are etched. If desired, a glass coverslip is used to fully enclose the channels. Also, holes are drilled in the glass to allow fluidic access. For straighter edges and a deeper etch depth, deep reactive ion etching (DRIE) can be used as an alternative to wet chemical etching.

In another embodiment of the invention, micro-channels may be formed on a silicon substrate using the following method. A seed layer of a metal, such as copper, is deposited over a surface of the substrate. Any suitable blanket deposition process may be used to deposit the seed layer of metal, such as physical vapor deposition (PVD), chemical vapor deposition (CVD), or other methods known to those skilled in the art. A layer of a sacrificial material, such as a dielectric material or a photoresist material, is then deposited over the seed layer. By removing the sacrificial material, for example using chemical etch process or thermal decomposition process, a number of trenches in the sacrificial layer is formed, and the seed layer is exposed in each of the trenches. Another layer of the metal, such as copper, is deposited over the exposed seed layer in the trenches. The metal layer extends over portions of the upper surface of the sacrificial layer; but gaps remain between the metal material layers extending from adjacent trenches and over the upper surface of the sacrificial layer. The sacrificial layer is removed, for example using chemical etching process or thermal decomposition process, and regions from which the sacrificial layer has been removed form channels in the metal layer. An additional layer of the metal is deposited over the upper surfaces of the metal layer to close the gaps over the channels.

In the embodiments of the invention, micro-channels and microfluidic devices can be made by using soft lithography method with suitable materials, such as silicon and polydimethylsiloxane (PDMS). With these techniques it is possible to generate patterns with critical dimensions as small as 30 nm. These techniques use transparent, elastomeric PDMS "stamps" with patterned relief on the surface to generate features. The stamps can be prepared by casting prepolymers against masters patterned by conventional lithographic techniques, as well as against other masters of interest. Several different techniques are known collectively as soft lithography. They are as described below:

Near-Field Phase Shift Lithography.

A transparent PDMS phase mask with relief on its surface is placed in conformal contact with a layer of photoresist. Light passing through the stamp is modulated in the near-field. Features with dimensions between 40 and 100 nm are produced in photoresist at each phase edge.

Replica Molding.

A PDMS stamp is cast against a conventionally patterned master. Polyurethane is then molded against the secondary PDMS master. In this way, multiple copies can be made without damaging the original master. The technique can replicate features as small as 30 nm.

Micromolding in Capillaries (MIMIC).

Continuous channels are formed when a PDMS stamp is brought into conformal contact with a solid substrate. Capillary action fills the channels with a polymer precursor. The polymer is cured and the stamp is removed. MIMIC is able to generate features down to 1 µm in size.

Microtransfer Molding ((TM).

A PDMS stamp is filled with a prepolymer or ceramic precursor and placed on a substrate. The material is cured and the stamp is removed. The technique generates features as small as 250 nm and is able to generate multilayer systems.

Solvent-Assisted Microcontact Molding (SAMIM).

A small amount of solvent is spread on a patterned PDMS stamp and the stamp is placed on a polymer, such as photoresist. The solvent swells the polymer and causes it to expand to fill the surface relief of the stamp. Features as small as 60 nm have been produced.

Microcontact Printing ((CP).

An "ink" of alkanethiols is spread on a patterned PDMS stamp. The stamp is then brought into contact with the substrate, which can range from coinage metals to oxide layers. The thiol ink is transferred to the substrate where it forms a self-assembled monolayer that can act as a resist against etching. Features as small as 300 nm have been made in this way.

Techniques used in other groups include micromachining of silicon for microelectricalmechanical systems, and embossing of thermoplastic with patterned quartz. Unlike conventional lithography, these techniques are able to generate features on both curved and reflective substrates and rapidly pattern large areas. A variety of materials could be patterned using the above techniques, including metals and polymers. The methods complement and extend existing nanolithographic techniques and provide new routes to high-quality patterns and structures with feature sizes of about 30 nm.

Standard lithography on silicone wafer or silica glass could also be used to fabricate the devices of the embodiments of this invention. Chambers or channels in the micrometer or nanometer scale can be fabricated from the devices, fluidic flow can be controlled by pressure gradient, electrical field gradient, gravity, and heat gradient. The binding complexes or sensors can also be separated by planar device with a single a plurality of chambers, where the surfaces are modified with polymers (polyethylene glycol (PEG)-dramatized compounds) that can minimize non-specific binding. The solid support can be inorganic material (e.g., glass, ceramic) or metal (e.g., aluminum), biomolecules, protein, antibody, nucleic acid can be coated on the surface for specific analyte binding.

In the embodiments of the invention, the micro-channels formed on the substrate may be straight or have angles or curves along their lengths. The characteristics and layout of the micro-channels are determined by the specific applications the device is designed for. Although straight micro-channels lining next to one another are a typical design for microfluidic devices, the micro-channels in the embodiments of the invention may be designed in many different patterns to serve specific separation and detection requirements. Further, in the embodiments of the invention, the cross-section of the micro-channel so formed may be uniform or vary along the channel's length, and may have various shapes, such as rectangle, circle, or polygon.

In one embodiment of the invention, the micro-channel comprises at least one straight segment and has a cross-section comprising a rectangle. The rectangular cross-section of the micro-channel has a height and width of between about 0.1 µm and 500 µm. The micro-channel's cross-section dimension is determined by the specific applications that the device is designed for. Although embodiments of the invention typically comprise micro-channels with cross-section height and width dimensions from about 1 µm to 100 µm, or from about 10 µm to 50 µm, other dimensions are also encompassed by the invention. For example, when used for separation or detection of blood cells, such as red or white blood cells, a dimension of at least 10 µm by 10 µm should be used. On the other hand, when used for separation or detection of antibodies or viruses, micro-channels with cross-section dimension in sub-microns or nanometers can be used.

In the embodiments of the invention, the micro-channel comprises at least two openings for fluid communication. The openings serve for inlet, outlet, vent, or other purposes, such that fluids may pass through or stay within the channel as desired. Although the openings are typically located at an end of the micro-channel, they may be situated at any part of the channel to facilitate specific needs. The openings are designed such that they are suitable for connection with connectors, other devices or equipment to facilitate fluid communications as desired.

In one embodiment of the invention, the device comprises an inlet fluid reservoir in fluid communication with at least one of the openings of the micro-channel; and an outlet fluid reservoir in fluid communication with at least one of the openings of the micro-channel. The reservoirs serve to facilitate fluid flow through the micro-channel. Further, in certain situations, multiple micro-channels may share one or more reservoirs. For example, the inlets of the multiple channels may share a reservoir and the outlets of the multiple channels may share another reservoir.

The embodiments of the present invention also encompass a magnetic stripe that extends along the length of the micro-channel and is formed in association with the micro-channel. A function of the magnetic stripe is to be used to create a magnetic field along at least a portion of the micro-channel to effectuate the separation of cells and biomolecules.

Materials suitable for use as the magnetic stripe for the embodiments of the invention include permanent magnetic materials, ferromagnetic materials, paramagnetic materials, and non-magnetic metals. When a ferromagnetic material is used for the magnetic stripe, an external magnetic field is used to magnetize the stripe. Further, when either a ferromagnetic or non-magnetic material is used for the magnetic stripe, an electrical current is applied to the stripe to create an electromagnet. In one embodiment of the invention, the magnetic stripe comprises one or more of iron, nickel, cobalt, copper, aluminum, and mixtures thereof. Any suitable blanket deposition process may be used to form the magnetic stripe on the substrate, such as sputter coating, physical vapor deposition (PVD), chemical vapor deposition (CVD), or other methods known to those skilled in the art.

In the embodiments of the invention, the dimension of the magnetic stripe varies according to the specific application the device is designed for. Factors for the determination of the magnetic stripe's dimension include the magnetic force and field the magnetic stripe is desired to create, the material used, and the dimension of the micro-channel that the magnetic stripe is associated with. In one embodiment, the magnetic stripe has a thickness of between 0.5 µm and 10 µm, or more specifically, of between 1.0 µm and 3.0 µm. In another embodiment, the magnetic stripe has a width of between 0.1 µm and 50 µm, and more specifically, a width of between 1.0 µm and 20 µm. Although the length of the magnetic stripe is usually commensurate with the length of the associated micro-channel, the length of the magnetic stripe may vary, e.g., longer or shorter than the length of the channel, according to the specific needs and design of the device.

In one embodiment of the invention, the micro-channel is straight and has a rectangular cross-section; and a magnetic stripe is formed at approximately the center of a side of the rectangle. More specifically, no more than one magnetic stripe is formed on the inside surface of the micro-channel or on said surface of the substrate adjoining the micro-channel.

In the embodiments of the invention, the magnetic stripes are "in association with" or "associated with" the micro-channels such that the magnetic effect of a magnetic stripe is effectively used to achieve separation of biomolecules and cells within the associated micro-channel. In other words, each micro-channel is associated with one or more magnetic stripes so that the separation of biomolecules or cells with the micro-channel is facilitated by the associated magnetic stripes. On the other hand, each magnetic stripe is also associated with one or more micro-channels so that the magnetic stripe is capable of facilitating the separation of biomolecules and cells with the micro-channels. An effective arrangement of a magnetic stripe in relation to a micro-channel is to form the magnetic stripe on an inside surface of the micro-channel or on the surface of the substrate adjoining the micro-channel.

In a specific embodiment of the invention, at least one micro-channel is associated with not more than one magnetic stripe. In another embodiment, at least one metal stripe is associated with not more than one micro-channel. The embodiment also encompasses situations where a plurality of micro-channels are each associated with not more than one magnetic stripe. In such embodiments of the invention, the fluid dynamics in each of the micro-channels and the magnetic properties and effects of each of the magnetic stripes can be individually controlled. This not only allows specific monitoring and separation of cells and biomolecules, down to a single cell, biomolecule, or a fragment thereof, but also allows multiple monitoring and separation of cells and biomolecules to be carried out simultaneously. In such situations, the embodiments of the invention can be further assisted and enhanced by integrating the micro-channels and the associated magnetic stripes into another device, such as an integrated circuit.

In one embodiment of the invention, a straight micro-channel with a rectangular cross-section and associated with one or more magnetic stripe on a silicon substrate is fabricated according to the following method. A straight groove with a rectangular cross-section is etched on the surface of the silicon substrate. The depth and width of the groove are commensurate with the thickness and width, respectively, of the magnetic stripe to be formed. For example, the depth of the channel may range from about 0.5 µm to 10 µm; and the width of the channel may range from about 1.0 µm to 50 µm. A ferromagnetic metal, such as nickel or iron, or a non-magnetic metal, such as copper, is then sputter coated onto the surface, including the groove, of the substrate. The coated surface is then polished, chemically and/or mechanically, such that only the metal within the groove remains on the substrate's surface to form a magnetic stripe and that the exposed surface of the magnetic stripe and the surface of the substrate form a single surface. The exposed surface of the magnetic stripe and the adjacent surface of the substrate may be passivated, if desired. A straight micro-channel with a rectangular cross-section is then formed around the magnetic stripe using methods disclosed herein. The micro-channel comprises silicon, silicon polymers, such as polydimethylsiloxane, or one or more metals.

Another embodiment of the invention relates to a method for separation of cells and biomolecules using magnetism and microfluidic technologies. The method comprises: (1) providing a device that comprises a substrate, a closed micro-channel having at least two openings for fluidic communication formed on a surface of the substrate, and a magnetic stripe extending along the length of the micro-channel and formed on an inside surface of the micro-channel or on said surface of the substrate adjoining the micro-channel: (2) creating a magnetic field around the magnetic stripe; and (3) flowing liquid containing magnetically tagged biomolecules or cells through the micro-channel.

As disclosed herein, the magnetic stripe may comprise a permanent magnetic material, a ferromagnetic material, a paramagnetic material, or a non-magnetic material. In the case of a ferromagnetic material, such as nickel, iron, and cobalt, the magnetic stripe may be magnetized by applying an external magnetic field. When using a non-magnetic material, such as copper or aluminum, or a ferromagnetic material, the magnetic stripe may be turned into an electromagnet by flowing electrical current through the magnetic stripe. The appropriately magnetized magnetic stripe is then used to separate magnetically tagged biomolecules flowing inside the micro-channel associated with the magnetic stripe and within the magnetic field of the magnetic stripe. When necessary, the magnetization may be stopped by turning off the electricity, in the case of electromagnet, or applying a counter-balancing external magnetic field to demagnetize the ferromagnet or to annul the attractions between the magnetic stripe and the magnetically tagged biomolecules.

In one embodiment of the invention, one or more of the magnetically tagged biomolecules or cells are attracted to the magnetic stripe and separated from the rest of the liquid. In such a case, the one or more magnetically tagged biomolecules or cells are attracted to the magnetic stripe due to the magnetic forces between the biomolecules or cells and the stripe. The biomolecules or cells are thus trapped, dragged, slowed down, or otherwise attracted to the magnetic stripe such that the molecules or cells are separated from the main flow. In certain cases, the magnetically tagged biomolecules or cells are attached to the magnetic stripe. In such case, rinse or other type of washing may be applied with the micro-channel to wash out the non-attached fluid and the remaining biomolecules or cells may be separately collected or detected.

In another embodiment, a straight micro-channel is associated with a straight magnetic stripe, and the two are situated, or patterned, such that the micro-channel and the magnetic stripe are not parallel, but form an angle with each other. In the embodiment, when a magnetically tagged cell or biomolecule is attracted to, or trapped by, the magnetic stripe, it will flow along the direction of the magnetic stripe and deviate from the rest of the fluid, which flows along the direction of the micro-channel. The deviated cell or biomolecule is thus separated and/or detected.

In the embodiments of the invention, biological cells and biomolecules may be magnetically tagged using various methods. For example, paramagnetic materials, such as iron oxide ($Fe_2O_3$) may be used to tag the cells and biomolecules. Dextran or other polymer beads may be impregnated, or dispersed, with iron oxide and used as magnetic labels for cells and biomolecules. The beads may be coated, or combined, with appropriate antibodies before being tagged onto the target cells or biomolecules. One type of magnetic labels can be used in the embodiments of the invention is superparamagnetic Dynabeads® (M-280), which are polymer beads with an even dispersion of $Fe_2O_3$. The beads typically have relatively spherical shapes and mean diameters range from 1 µm to 10 µm.

In another embodiment of the present invention, the biological cells and biomolecules are magnetically tagged using magnetic nanoparticles, such as high-moment and/or single-domain magnetic nanoparticles. Such magnetic nanoparticles may be made from ferromagnetic materials such as iron, cobalt, nickel, and compounds and alloys containing such materials, and have mean diameters of between approximately 10 nm to 1000 nm. Since the size of such nanoparticle magnetic tags are comparable to many of the target biomolecules, such as DNA fragments, it is possible to achieve one target per tag, providing highly specific and efficient separation and detection using the embodiments of the present invention.

FIG. 1 illustrates an embodiment of the invention. As shown, a magnetic stripe (straight metal line) was formed on an inside surface of a micro-channel. The micro-channel was straight with a rectangular cross-section, and the magnetic stripe was located near the center of one side of the rectangle. The inside surface of the micro-channel and exposed surface of the magnetic stripe were passivated. In the top-down view, an electrical current was flown from left to right, creating a magnetic field surrounding the magnetic stripe, as shown in both the top-down and cross-section views. A liquid containing a magnetic particle (Dynabead M-280) was flown through the micro-channel from left to right, as shown in the top-down view.

As shown in FIG. 1, as the magnetic particle flows through the micro-channel, an electrical current through the magnetic stripe (straight metal line) is needed to create a magnetic force that counter-balances the drag force for, attracts, stops, or traps, the flowing particle. Assuming that the flowing liquid is whole blood at a rate of 100 µm/second, and that the magnetic particle is spherical with a diameter of 10 µm, a drag force of 28 pN (PicoNewton) on the particle can be calculated using Stokes Formula. In other words, to trap, or stop, the flowing magnetic particle, necessary electrical current is needed to counter-balance a drag force of 28 pN. Table 1 shows the electrical current needed to counter-balance a drag force of 28 pN for the magnetic particle at different distances from the magnetic stripe.

TABLE 1

Calculated electrical current needed to counter-balance a drag force of 28 pN for a spherical magnetic particle having a diameter of 10 µm and flowing at a rate of 100 µm/second.

| Distance between Particle and Magnetic Stripe | Electrical Current Needed |
| --- | --- |
| 5 µm | 25 mA |
| 10 µm | 99 mA |
| 15 µm | 222 mA |

As demonstrated in FIG. 1 and Table 1, according to the embodiments of the invention, appropriate controls and manipulations can be performed, in terms of the characteristics of the magnetically tagged biomolecules or cells, the fluid dynamics of the liquid, the dimensions of the micro-channels and the magnetic stripes, and the magnetic properties of the magnetic stripes, such that the movement of the magnetically tagged biomolecules or cells can be measured and detected.

Another embodiment of the invention relates to a method of detecting biological cells and biomolecules using a magnetic tunnel junction sensor. The method comprises providing a magnetic tunnel junction sensor that comprises two ferromagnetic metal layers separated by an insulating layer; providing a magnetically tagged biomolecule or cell; exposing the magnetic tunnel junction sensor to the magnetically tagged biomolecule; and measuring the magnetoresistance of the magnetic tunnel junction sensor.

Another embodiment of the invention relates to a device with functions of a magnetic tunnel junction and capable of detecting magnetically tagged biomolecules and/or cells. The device comprises two ferromagnetic metal layers separated by an insulating layer and is capable of functioning as a magnetic tunnel junction wherein the magnetoresistance of the junction changes when the device is exposed to a magnetically tagged biomolecule or cell.

Yet another embodiment of the invention relates to a method of making a device, which is capable of functioning as a magnetic tunnel junction and that the magnetoresistance of the device changes when the device is exposed to a magnetically tagged biomolecule or cell. The method comprises depositing a first ferromagnetic metal layer on a substrate; depositing an insulating layer over the first ferromagnetic metal layer; and depositing a second ferromagnetic metal layer over the insulating layer. In specific embodiments of the invention, the method further comprises depositing an adhesive layer over the substrate prior to depositing the first ferromagnetic metal layer. In another embodiment of the invention, the method further comprises depositing an anti-ferromagnetic layer prior to depositing the first ferromagnetic metal layer.

In one embodiment of the invention, the magnetic tunnel junction sensor is based, or fabricated, on a silicon substrate. More specifically, the magnetic tunnel junction sensor can be integrated into an integrated circuit. Further, the silicon substrate may comprise micro-arrays or microfluidic channels, wherein the magnetic tunnel junction sensor can be used to detect the presence of analytes, such as biological cells or biomolecules, in conjunction with the micro-arrays and the microfluidic channels.

In one embodiment of the invention, the two ferromagnetic layers of the magnetic tunnel junction sensor each independently comprise one or more of nickel, iron, and cobalt. The two ferromagnetic metal layers each have a thickness of between 1 nm and 500 nm. More specifically, the two ferromagnetic metal layers each have a thickness of between 5 nm and 50 nm.

In another embodiment of the invention, one of the ferromagnetic layers is referred to as the top ferromagnetic layer or top electrode, and usually comprises a soft ferromagnetic material. The other ferromagnetic layer is referred to as the bottom ferromagnetic layer or the bottom electrode. The top ferromagnetic layer may be passivated or protected by a layer of coating, especially in case where the top electrode is often exposed, such as to liquid containing the target.

In the embodiments of the invention, any suitable materials may be used as the insulating layer. Specific materials that can be used as the insulating layer include oxide and nitride based materials. In one embodiment, the insulating layer comprises $Al_2O_3$ or MgO. In another embodiment, the insulating layer has a thickness of between 0.1 nm and 10 nm, or more specifically, between 0.5 nm and 5 nm.

In one embodiment of the invention, the magnetic tunnel junction sensor further comprises an anti-ferromagnetic coupling layer. The anti-ferromagnetic coupling layer may be combined with the bottom ferromagnetic layer, forming an anti-ferromagnetic/ferromagnetic bi-layer that serves as a magnetically pinned bottom electrode. Such a magnetically pinned bottom electrode is capable of stabilizing magnetic domains during the detection. In specific embodiments of the invention, the anti-ferromagnetic coupling layer comprises one or more of IrMn, NiMn, FeMn, and NiO.

In another embodiment of the invention, the magnetic tunnel junction sensor is based on a silicon substrate and is joined with the silicon substrate by an adhesive layer. The adhesive layer can also be referred to and regarded as a seed layer used to join the magnetic tunnel junction sensor with the substrate. In a specific embodiment, the bottom ferromagnetic layer or the anti-ferromagnetic coupling layer is joined with the silicon substrate by the adhesive layer. Any suitable adhesive materials may be used as the adhesive layer. In one embodiment of the invention, the adhesive layer comprises one or more of titanium, tantalum, platinum, and palladium.

Another embodiment of the invention relates to a device that comprises a substrate and a plurality of magnetic tunnel junction sensors, wherein each of the plurality of magnetic tunnel junction sensors comprises two ferromagnetic metal layers separated by an insulating layer and is formed on or near a surface of the substrate. Therefore, variations of the embodiment encompass a microarray or macroarray of magnetic tunnel junction sensors on the substrate. The magnetic tunnel junction sensors may be formed on or near the surface of the substrate using methods disclosed herein. Materials for the substrate include, but not limited to, silicon, glass, and a polymeric material.

In one embodiment, each of the plurality of magnetic tunnel junction sensors on the substrate further comprises an anti-ferromagnetic coupling layer. Further, an adhesive layer may be used to fabricate the magnetic tunnel junction sensors on the surface of the substrate. A specific layout of a magnetic tunnel junction sensor on the substrate includes, from the surface of the substrate, an adhesive layer or seed layer, an anti-ferromagnetic coupling layer, a bottom ferromagnetic layer or bottom electrode, an insulating layer, and a top ferromagnetic layer or top electrode. The top electrode may be exposed on the surface of the device or protected by a thin protective layer.

In another embodiment, the magnetic tunnel junction sensors are capable of detecting magnetically tagged biomolecules on or near the surface of the substrate. In one embodiment, each of the plurality of magnetic tunnel junction sensors is associated with a biomolecule, such as a DNA or protein. The association may be through surface functionalization techniques disclosed herein.

After association of DNAs to the plurality of magnetic tunnel junction sensors on the surface of the substrate, a DNA microarray is formed and can be used to perform multiple DNA analysis. In such cases, the complementary DNAs are magnetically tagged and capable of being detected by at least one of the magnetic tunnel junction sensors.

Another embodiment of the invention relates to a method that comprises: (1) providing a device that comprises a substrate and a plurality of magnetic tunnel junction sensors, wherein each of the plurality of magnetic tunnel junction sensors comprises two ferromagnetic metal layers separated by an insulating layer and is formed on or near a surface of the substrate; (2) associating a first biomolecule with each of the plurality of magnetic tunnel junction sensors; (3) providing a magnetically tagged second biomolecule; (4) contacting the surface of the device with the magnetically tagged second biomolecule; and (5) measuring the magnetoresistance of each of the plurality of magnetic tunnel junction sensors. In one embodiment, the first and second biomolecules are DNAs. In another embodiment, the second biomolecule is tagged with a magnetic nanoparticle.

The above embodiments of the invention may also be regarded as integrating the plurality of magnetic tunnel junction sensors into a microarray, such as a DNA array. In the embodiments, as discussed herein, multiple magnetic tunnel junction sensors are attached on the surface of the substrate and form a microarray and used as detectors for magnetically tagged molecules or fragments of molecules. When incorporated into a DNA microarray, the magnetic tunnel junction sensors are further combined with the first biomolecule, or the probe molecule or DNA probe, such that, when the second biomolecule, or the DNA target, and the probe hybridized, the target molecule, such as a DNA target, can be detected through the target's magnetic interactions with the magnetic tunnel junction sensor.

The microarray devices of the embodiments of the invention may be formed by any suitable means of manufacture, including semiconductor manufacturing methods, microforming processes, molding methods, material deposition methods, etc., or any suitable combination of such methods. In certain embodiments one or more of the magnetic tunnel junction sensors, electrodes and/or the pad may be formed via semiconductor manufacturing methods on a semiconductor substrate. Thin film inorganic coatings may be selectively deposited on portions of the substrate and/or pad surface. Examples of suitable deposition techniques include vacuum sputtering, electron beam deposition, solution deposition, and chemical vapor deposition. The inorganic coatings may perform a variety of functions. For example, the coatings may be used to increase the hydrophilicity of a surface or to improve high temperature properties. Conductive coatings may be used to form magnetic tunnel junction sensor electrodes. Coatings may be used to provide a physical barrier on the surface, e.g. to retain fluid at specific sites on the surface. The microarray devices used in the present invention may be fabricated according to procedures well-known in the arts of microarray and semiconductor device manufacturing.

In some embodiments the probes may be selected from biomolecules, such as polypeptides, polynucleotides, glycoproteins, polysaccharides, hormones, growth factors, peptidoglycans, or the like. The probe could be natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. In embodiments employing oligonucleotide probes, the probes may be synthesized, in situ, on the surface of the pad in either the 3' to 5' or 5' to 3' direction using the 3'-β-cyanoethyl-phosphoramidites or 5'-β-cyanoethyl-phosphoramidites and related chemistries known in the art. In situ synthesis of the oligonucleotides may also be performed in the 5' to 3' direction using nucleotide coupling chemistries that utilize 3'-photoremovable protecting groups. Alternatively, the oligonucleotide probes may be synthesized on the standard controlled pore glass (CPG) in the 3' to 5' direction using 3'-β-cyanoethyl-phosphoramidites and related chemistries and incorporating a primary amine or thiol functional group onto the 5' terminus of the oligonucleotide. The oligonucleotides may then be covalently attached to the pad surface via their 5' termini using thiol or amine-dependent coupling chemistries known in the art. The density of the probes on the surface can range from about 1,000 to 200,000 probe molecules per square micron. The probe density can be controlled by adjusting the density of the reactive groups on the surface of the pad for either the in situ synthesis or post-synthesis deposition methods. Other suitable means for synthesis of probe as are known in the art may be employed.

The oligonucleotide probes include, but are not limited to, the four natural deoxyribonucleotides; deoxythymidylic acid, deoxycytidylic acid, deoxyadenylic acid and deoxyguanylic acid. The probes can also be ribonucleotides, uridylic acid, cytidylic acid, adenylic acid, and guanylic acid. Modified nucleosides may also be incorporated into the oligonucleotide probes. These include but are not limited to; 2'-deoxy-5-methylcytidine, 2'-deoxy-5-fluorocytidine, 2'-deoxy-5-iodocytidine, 2'-deoxy-5-fluorouridine, 2'-deoxy-5-iodouridine, 2'-O-methyl-5-fluorouridine, 2'-deoxy-5-iodouridine, 2'-deoxy-5(1-propynyl)uridine, 2'-O-methyl-5(1-propynyl)uridine, 2-thiothymidine, 4-thiothymidine, 2'-deoxy-5(1-propynyl)cytidine, 2'-O-methyl-5(1-propynyl)cytidine, 2'-O-methyladenosine, 2'-deoxy-2,6-diaminopurine, 2'-O-methyl-2,6-diaminopurine, 2'-deoxy-7-deazadenosine, 2'-deoxy-6methyladenosine, 2'-deoxy-8-oxoadenosine, 2'-O-methylguanosine, 2'-deoxy-7-deazaguanosine, 2'-deoxy-8-oxoguanosine, 2'-deoxyinosine or the like.

The polynucleotide probes can vary in length from a range of about 5 to about 100 nucleotides, such as about 8 to about 80 nucleotides, such as about 10 to about 60 nucleotides, and such as about 15 to about 50 nucleotides. Longer polynucleotide probes are typically employed for applications where the sample contains a high sequence-complexity target mixture. Shorter polynucleotide probes are typically employed in applications where single nucleotide discrimination, such as mutation detection, is desired.

The target molecule could be a nucleic acid such as genomic DNA, genomic RNA, messenger RNA, ribosomal RNA or transfer RNA, an oligonucleotide or polynucleotide of DNA or RNA generated by enzymatic process such as PCR or reverse transcription, or any synthetic DNA, RNA, or any other desired nucleic acid or any combination thereof. The target molecule may be double stranded or single stranded. It is preferred that the target molecule be single stranded in order to increase the efficiency of its interaction with the probe sequences. The target molecule could contain nanomaterials such a carbon nanotube, wherein the nanomaterial such as the carbon nanotube could be functionalized at its ends to molecules containing nucleic acid. The target molecules can be magnetically tagged, e.g., with magnetic nanoparticle, using methods disclosed herein.

The architecture of the array probes may be either generic or specific with regard to the complementary target sequences that it may hybridize with. For example, an array of all possible 7-mer probe sequences could be used to interrogate targets having any sequence. The advantage of such an array is that it is not application specific and therefore generic. Alternatively, the probe array may contain polynucleotide sequences that are complementary to a specific target sequence or set of target sequences and individual or multiple mutations thereof. Such an array is useful in the diagnosis of specific disorders, which are characterized by the presence of a particular nucleic acid sequence. For example, the target sequence may be that of a particular exogenous disease causing agent, e.g. human immunodeficiency virus, or alternatively the target sequence may be that portion of the human genome which is known to be mutated in instances of a particular disorder, e.g., sickle cell anemia or cystic fibrosis, or to a portion of a genome known to be associated with certain phenotypes, e.g., resistance to certain drugs, overreactivity to certain drugs, or even susceptibility to side-effects of certain drugs.

In one embodiment of the present invention, polymers on a plurality of dies on a wafer substrate are functionalized on the magnetic tunnel junction sensors or electrodes as follows. First, a terminal end of a monomer, nucleotide, or linker molecule (i.e., a molecule which "links," for example, a monomer or nucleotide to a substrate) is provided with at least one reactive functional group, which is protected with a protecting group removable by an electrochemically generated reagent. The protecting group(s) is exposed to reagents electrochemically generated at magnetic tunnel junction sensor or the electrode and removed from the monomer, nucleotide or linker molecule in a first selected region to expose a reactive functional group. The substrate is then contacted with the monomer or a pre-formed molecule (called the first molecule) such that the surface bonds with the exposed functional group(s) of the monomer or the pre-formed molecule. The first molecule may also bear at least one protected chemical functional group removable by an electrochemically generated reagent. The monomer or pre-formed molecule can then be deprotected in the same manner to yield a second reactive chemical functional group. A different monomer or pre-formed molecule (called the second molecule), which may also bear at least one protecting group removable by an electrochemically generated reagent, is subsequently brought in the vicinity of the substrate to bond with the second exposed functional group of the first molecule. Any unreacted functional group can optionally be capped at any point during the synthesis process. The deprotection and bonding steps can be repeated sequentially at the plurality of the predefined regions on the substrate until polymers or oligonucleotides of a desired sequence and length are obtained.

In another embodiment of the present invention, polymers on a plurality of dies on a wafer substrate are functionalized on the magnetic tunnel junction sensors or the electrodes as follows. First, a substrate of a wafer having one or more molecules bearing at least one protected chemical functional group bonded on an array of electrodes on a plurality of dies is obtained. The array of electrodes is contacted with a buffering or scavenging solution. Following application of an electric potential to selected electrodes in the array of magnetic tunnel junction sensors or electrodes sufficient to generate electrochemical reagents capable of deprotecting the protected chemical functional groups, molecules on the array of magnetic tunnel junction sensors or electrodes are deprotected to expose reactive functional groups, thereby preparing them for bonding. A monomer solution or a pre-formed molecule (called the first molecule), such as proteins, nucleic acids, polysaccharides, and porphyrins, is then contacted with the substrate surface of the wafer and the monomers or pre-formed molecules are bonded in parallel with a plurality of deprotected chemical functional groups on a plurality of dies on the wafer. Another sufficient potential is subsequently applied to select electrodes in the array to deprotect at least one chemical functional group on the bonded molecule or another of the molecules bearing at least one protected chemical functional group on a plurality of dies on the wafer. A different monomer or pre-formed molecule (called the second molecule) having at least one protected chemical functional group is subsequently attached to a deprotected chemical functional group of the bonded molecule or the other deprotected molecule located at a plurality of dies of the wafer. The selective deprotection and bonding steps can be repeated sequentially until polymers or oligonucleotides of a desired sequence and length are obtained. The selective deprotection step is repeated by applying another potential sufficient to effect deprotection of a chemical functional group on a bonded protected monomer or a bonded protected molecule. The subsequent bonding of an additional monomer or pre-formed molecule to the deprotected chemical functional group(s) until at least two separate polymers or oligonucleotides of desired length are formed on the substrate.

An embodiment of the invention relates to generating multiplex data and analyzing the resulting data. The embodiment of the invention can be used to collect information from multiple binding complexes in a single measurement; normally a separation step is used before any detection.

The array chip could also be used for therapeutic materials development, i.e., for drug development and for biomaterial studies, as well as for biomedical research, analytical chemistry, high throughput compound screening, and bioprocess monitoring. An exemplary application includes applications in which various known ligands for particular receptors can be placed on the array chip and hybridization could be performed between the ligands and labeled receptors.

Another application of the array chip of an embodiment of this invention includes, for example, sequencing genomic DNA by the technique of sequencing by hybridization. Non-biological applications are also contemplated, and include the production of organic materials with varying levels of doping for use, for example, in semiconductor devices. Other examples of non-biological uses include anticorrosives, antifoulants, and paints.

It is specifically contemplated that the array chip and/or the methods of manufacturing the array chip of an embodiment of the invention could be used for developing new materials, particularly nanomaterials for many purposes including, but not limited to corrosion resistance, battery energy storage, electroplating, low voltage phosphorescence, bone graft compatibility, resisting fouling by marine organisms, superconductivity, epitaxial lattice matching, or chemical catalysis. Materials for these or other utilities may be formed proximate to one or a plurality of the electrodes in parallel on a plurality of dies of a silicon wafer, for example. Alternatively, materials may be formed by modifying the surface of one or a plurality of electrodes on a plurality of dies by generating reagents electrochemically.

It is further contemplated that an array chip of the embodiments of the invention could be used to develop screening methods for testing materials. That is, reagents electrochemically generated by an electrode on a die could be used to test the physical and chemical properties of materials proximate to the electrode. For example, the array chip could be used for testing corrosion resistance, electroplating efficiency, chemical kinetics, superconductivity, electro-chemiluminescence and catalyst lifetimes.

Figure 2:
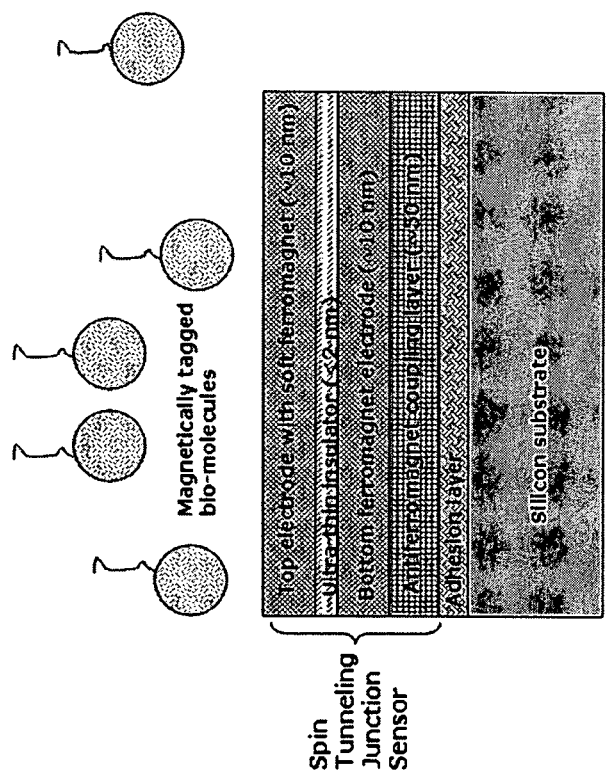
FIG. 2 shows a schematic of a spin tunneling junction sensor for detecting magnetically tagged biomolecules.

FIG. 2 illustrates an embodiment of the invention, in which a silicon based magnetic tunnel junction sensor is used to detect magnetically tagged biomolecules. As shown, the magnetic tunnel junction sensor, or spin tunneling junction sensor, comprises a top electrode with soft ferromagnet, an ultra-thin insulating layer, a bottom ferromagnet electrode, and an anti-ferromagnet coupling layer. The magnetic tunnel junction sensor is attached to the silicon substrate through an adhesion layer. As shown, both the top and bottom electrode have a thickness of approximately 10 nm. The ultra-thin insulator layer has a thickness of approximately 2 nm; and the anti-ferromagnetic coupling layer has a thickness of approximately 50 nm. If necessary, the top electrode may be passivated, or coated with a protection layer (not shown). In applications, the magnetic tunnel junction sensor is so situated such that the sensor is exposed to the magnetically tagged biomolecules or cells, or the magnetic fields of the biomolecules or cells. Upon magnetic interactions between the magnetic tunnel junction sensor and the magnetically tagged biomolecule or cell, changes in the magnetoresistance of the magnetic tunnel junction sensor are measured, indicating the presence of the magnetically tagged biomolecule or cell.

Figure 3:
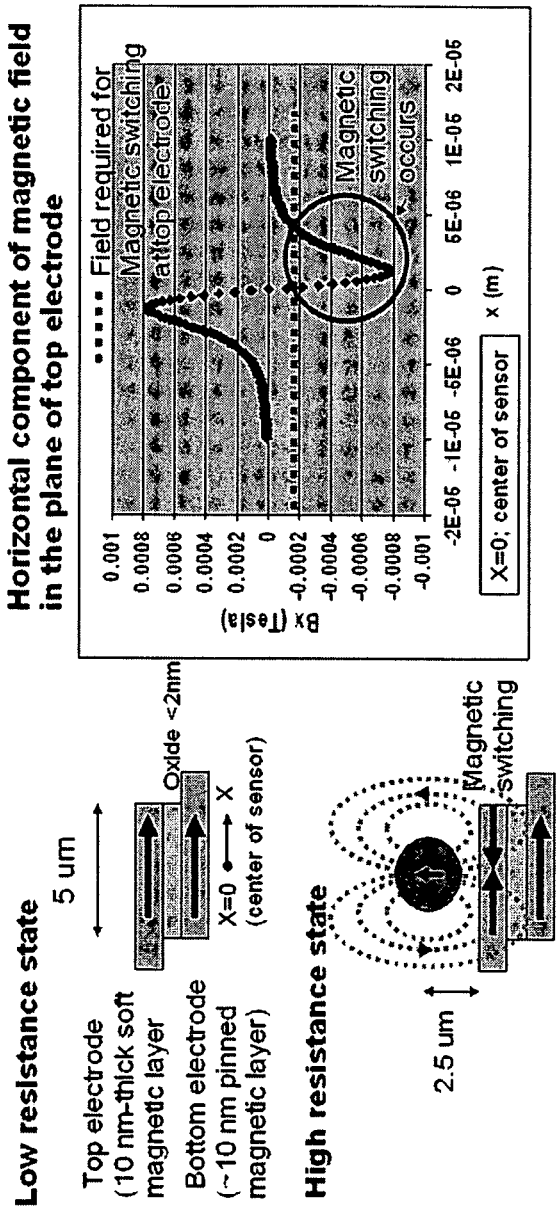
FIG. 3 shows a schematic of detecting a single magnetic particle using a spin tunneling junction sensor.

FIG. 3 illustrates the detection of a single magnetic particle using an embodiment of the magnetic tunnel junction sensor of the invention. As shown, a magnetic tunnel junction sensor with a dimension of approximately 5 μm is used to detect a magnetic particle with a diameter of approximately 3 μm and a volume magnetization of approximately 10 kA/m. The magnetic tunnel junction sensor comprises a top electrode with a soft ferromagnetic layer of approximately 10 nm thick and a bottom electrode with a pinned ferromagnetic layer of approximately 10 nm. An insulating layer of approximately 2 nm thick and comprising aluminum oxide ($Al_2O_3$) is in between the two electrodes.

As shown in FIG. 3, the magnetic tunnel junction sensor is in low resistance state when no magnetic particle is present near the sensor. When the particle is within the detectable range of the magnetic tunnel junction sensor, for example at a distance of approximately 2.5 μm from the center of the particle to the surface of the top electrode, magnetic switching at the top electrode occurs, as shown in FIG. 3.

Another embodiment of the invention relates to a system for separation and detection of biological cells and biomolecules. The system comprises a substrate; a closed micro-channel having at least two openings for fluidic communication and formed on a surface of the substrate; a magnetic stripe extending along the length of the micro-channel and formed on an inside surface of the micro-channel or on the surface of the substrate adjoining the micro-channel; a magnetic tunnel junction sensor formed on a surface of the substrate and comprising two ferromagnetic metal layers separated by an insulating layer.

Another embodiment of the invention relates to a method of separating and detecting biological cells and biomolecules. The method comprises: (1) providing a device that comprises a substrate, a closed micro-channel having at least two openings for fluidic communication and formed on a surface of the substrate, a magnetic stripe extending along the length of the micro-channel and formed on an inside surface of the micro-channel or on the surface of the substrate adjoining the micro-channel, and a magnetic tunnel junction sensor formed on a surface of the substrate and comprising two ferromagnetic metal layers separated by an insulating layer; (2) creating a magnetic field around the magnetic stripe; (3) flowing liquid containing a magnetically tagged biomolecule through the micro-channel; (4) exposing the magnetic tunnel junction sensor to the magnetically tagged biomolecule; and (5) measuring the magnetoresistance of the magnetic tunnel junction sensor.

Figure 4:
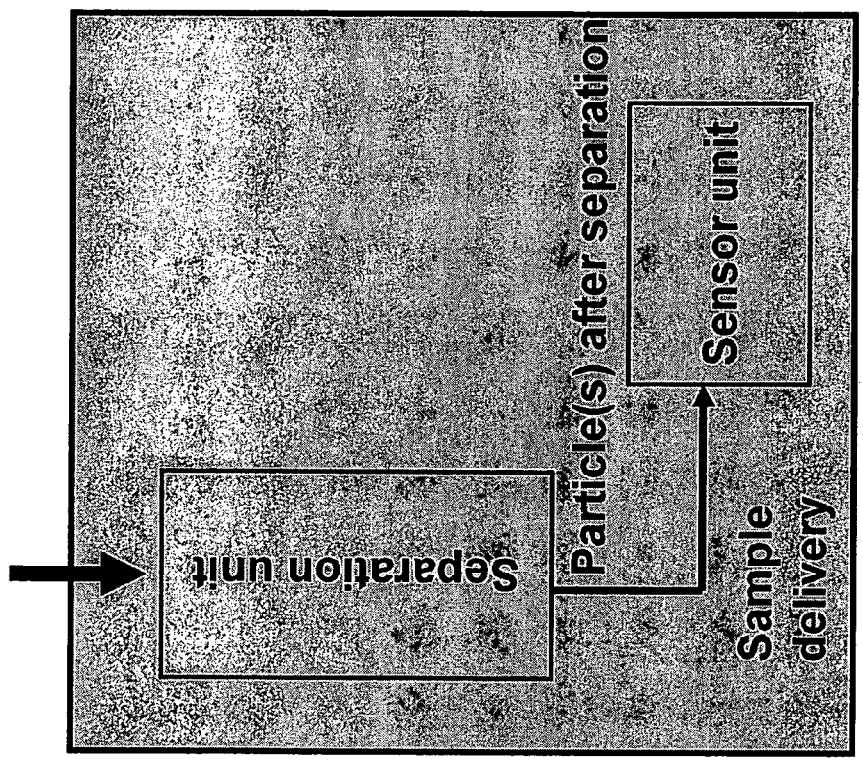
FIG. 4 shows a schematic of a system having a separation unit and a sensor unit in a single device.
Figure 5:
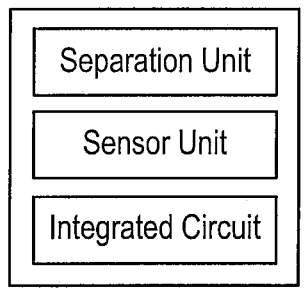
FIG. 5 is a schematic showing an alternative view of a system as shown in FIG. 4, the system having a separation unit and a sensor unit in a single device.

FIG. 4 illustrates an embodiment of the invention in which the separation and detection of biomolecules and/or cells are performed using a single system or device. As shown, the device, e.g., a microfluidic device or an integrated circuit, comprises a separation unit and a detection/sensor unit. A sample containing magnetically tagged biomolecules and/or cells is first flown into the separation unit. A part or the whole fluid coming out the separation unit is then flown into the sensor unit to undergo various detections.

In one embodiment of the invention, the separation unit comprises a microfluidic device disclosed herein. For example, the device comprises a substrate and a closed micro-channel formed on a surface of the substrate. The micro-channel has at least two openings for fluidic communication. The device further comprises a magnetic stripe that extends along the length of the micro-channel and is formed on an inside surface of the micro-channel or on the surface of the substrate adjoining the micro-channel. In this embodiment, the sensor unit could comprise any detection or sensing means suitable for detecting samples containing magnetically tagged biomolecules and/or cells.

In another embodiment of the invention, the sensor unit comprises a magnetic tunnel junction sensor as disclosed herein. For example, the magnetic tunnel junction comprises two ferromagnetic metal layers separated by an insulating layer. In this embodiment, the separation unit could be any suitable separation means that are capable of separating magnetically tagged biomolecules and/or cells.

As discussed herein, embodiments of the invention encompass the integration of the micro-channels and associated magnetic stripes for separation of biomolecules and cells and the magnetic tunnel junction sensors for detection of the biomolecules and cells into a single device, such that the separation and detection may be carried out in the same device. Further, the device may itself be an otherwise integrated device, such as a microarray device, a microfluidic device, or an integrated circuit. The functions of the micro-channels, the associated magnetic stripes and the magnetic tunnel junction sensors are added to and incorporated with the existing functions of the device such that the integrated device is capable of performing separation and detection of biomolecules and cells in a rapid, sensitive, target specific, highly parallel, and/or comprehensive manner.

The characteristics of some of the embodiments of the invention are illustrated in the Figures and examples, which are intended to be merely exemplary of the invention. This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A device comprising:
   a substrate;
   a closed micro-channel formed on a surface of the substrate, the micro-channel having at least two openings for fluidic communication; and
   a magnetic stripe formed in association with the micro-channel, the magnetic stripe extending along the length of the micro-channel, a magnetic tunnel junction sensor comprising two ferromagnetic layers separated by an insulating layer, or a ferromagnetic layer and an anti-ferromagnetic layer separated by an insulating layer, and
   wherein the device is configured to detect and/or measure the movement of magnetically tagged particles; wherein the closed micro-channel is associated with not more than one magnetic stripe.

2. The device of claim 1, wherein the substrate comprises silicon.

3. The device of claim 2, wherein the substrate comprises an integrated circuit die.

4. The device of claim 1, wherein the micro-channel comprises at least one straight segment and has a cross-section comprising a rectangle.

5. The device of claim 4, wherein the rectangle has a height of between 1.0 µm and 500 µm.

6. The device of claim 5, wherein the rectangle has a height of between 10 µm and 50 µm.

7. The device of claim 4, wherein the rectangle has a width of between 1.0 µm and 500 µm.

8. The device of claim 7, wherein the rectangle has a width of between 10 µm and 50 µm.

9. The device of claim 1, wherein the magnetic stripe comprises one or more of iron, nickel, cobalt, copper, aluminum, and mixtures thereof.

10. The device of claim 1, wherein the magnetic stripe has a thickness of between 0.1 µm and 10 µm.

11. The device of claim 10, wherein the magnetic stripe has a thickness of between 1.0 µm and 3.0 µm.

12. The device of claim 1, wherein the magnetic stripe has a width of between 0.1 µm and 50 µm.

13. The device of claim 12, wherein the magnetic stripe has a width of between 1.0 µm and 20 µm.

14. The device of claim 1, wherein the micro-channel is straight and has a cross-section that comprises a rectangle; and wherein the magnetic stripe is formed at the center of a side of the rectangle.

15. The device of claim 1, wherein the device further comprises an inlet fluid reservoir in fluid communication with at least one of the openings of the microchannel; and an outlet fluid reservoir in fluid communication with at least one of the openings of the micro-channel.

16. The device of claim 1, wherein the device is configured to detect and/or measure the movement of magnetically tagged particles by polarization, magnetic resistance, magne-toresistance, and/or tunneling magnetoresistance.

17. The device of claim 1, wherein the insulating layer has a thickness of between 0.1 nm and 10 nm.

18. The device of claim 1, wherein the insulating layer comprises —$Al_2O_3$ or MgO.

19. The device of claim 1, further comprising a molecular probe attached to the magnetic tunnel junction sensor.

20. A method comprising:
   providing a device of claim 1;
   creating a magnetic field around the magnetic stripe;
   flowing liquid containing magnetically tagged biomolecules or cells through the micro-channel,
   wherein the device is configured to detect and/or measure the movement of magnetically tagged particles.

21. The method of claim 20, wherein the magnetic field is created by connecting electrical current through the magnetic stripe.

22. The method of claim 20, wherein one or more of the magnetically tagged biomolecules or cells are attracted to the magnetic stripe and separated from the rest of the liquid.

23. The method of claim 20, wherein the insulating layer has a thickness of between 0.1 nm and 10 nm.

24. The method of claim 20, wherein the insulating layer comprises $Al_2O_3$— or MgO.

25. A method of making a device comprising:
   providing a substrate;
   fabricating a closed micro-channel on a surface of the substrate, the micro-channel having at least two openings for fluidic communication;
   fabricating a magnetic stripe in association with the micro-channel, the magnetic stripe extending along the length of the micro-channel,
   fabricating a magnetic tunnel junction sensor, the magnetic tunnel junction sensor comprising two ferromagnetic layers separated by an insulating layer, or a ferromagnetic layer and an anti-ferromagnetic layer separated by an insulating layer;
   wherein the device is configured to detect and/or measure the movement of magnetically tagged particles;
   wherein the fabricating of the closed micro-channel comprises:
   depositing a seed layer of a metal over a surface of the substrate;

depositing a layer of a sacrificial material over the seed layer;

forming a number of trenches in the sacrificial layer, wherein the seed layer is exposed in each of the trenches;

depositing a layer of the metal over the exposed seed layer in the trenches, the metal layer extending over portions of an upper surface of the sacrificial layer, wherein gaps remain between the metal material extending from adjacent trenches and over the upper surface of the sacrificial layer;

removing the sacrificial layer, wherein regions from which the sacrificial layer has been removed form channels in the metal layer; and depositing an additional layer of the metal over upper surfaces of the metal layer to close the gaps over the channels.

26. The method of claim 25, wherein the fabricating of the magnetic stripe comprises:

etching a straight groove on the surface of the substrate;

coating a ferromagnetic or a non-magnetic metal onto the surface of the substrate, including the groove; and polishing the coated surface, wherein only the metal within the groove remains on the surface of the substrate.

27. The method of claim 25, wherein a molecular probe is attached to the magnetic tunnel junction sensor.

28. The method of claim 25, wherein the insulating layer has a thickness of between 0.1 nm and 10 nm.

29. The method of claim 25, wherein the insulating layer comprises $Al_2O_3$— or MgO.

* * * * *